United States Patent [19]

Muncheryan

[11] Patent Number: 4,979,180
[45] Date of Patent: Dec. 18, 1990

[54] MODULAR INTERCHANGEABLE LASER SYSTEM

[76] Inventor: Arthur M. Muncheryan, 1735 N. Morningside St., Orange, Calif. 92667

[21] Appl. No.: 440,725

[22] Filed: Nov. 24, 1989

[51] Int. Cl.$^5$ .............................................. H01S 3/08
[52] U.S. Cl. ....................................... 372/92; 372/98; 372/75; 372/71; 372/108; 372/101; 372/107
[58] Field of Search ....................... 372/66, 69, 71, 75, 372/107, 108, 109

[56] References Cited

U.S. PATENT DOCUMENTS 4,730,335  3/1988  Clark et al. ........................... 372/75
4,731,795  3/1988  Clark et al. ........................... 372/108

*Primary Examiner*—Léon Scott, Jr.

[57] ABSTRACT

A modular interchangeable laser instrumentation system for applications in industrial processing, medical surgery and treatment, dental treatment, metrology, military applications, forensic investigation, micromachining, optical storage, spectroscopy, research and many other related applications. The system principally comprises a handheld stylus with interchangeable modules to produce various selected laser-radiation beams for any particular work as needed. Each module and the combined modular stylus is adapted to produce a particular type of laser beam for the intended project in hand, and as the modular section of one stylus is replaced by the modular section of another stylus, the generated laser beam assumes a different optical and spectral character, so as to be compatible with the work under process and characterized by the type of material and thickness thereof, texture, or human anatomical tissue of one kind or another, requiring different focus intensities and modal formats. In short, the laser system is a universal, operational device for use in numerous applications now requiring various specific laser systems to accomplish them.

30 Claims, 2 Drawing Sheets

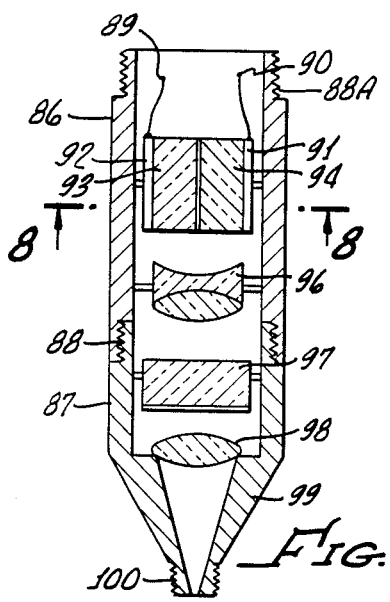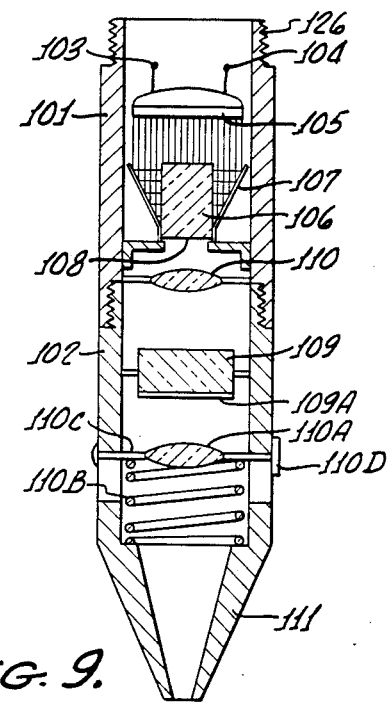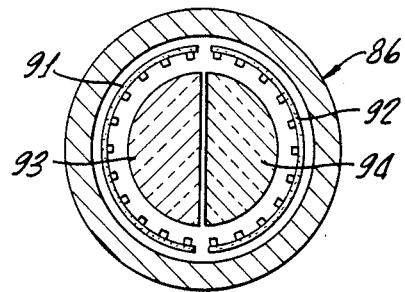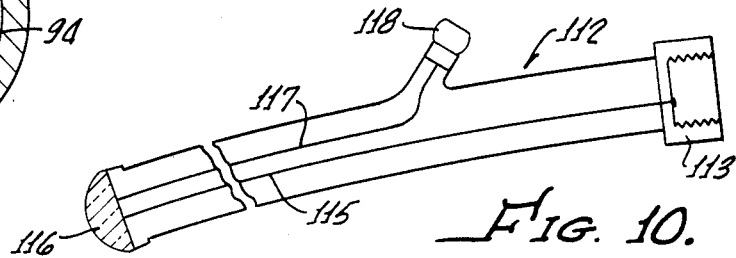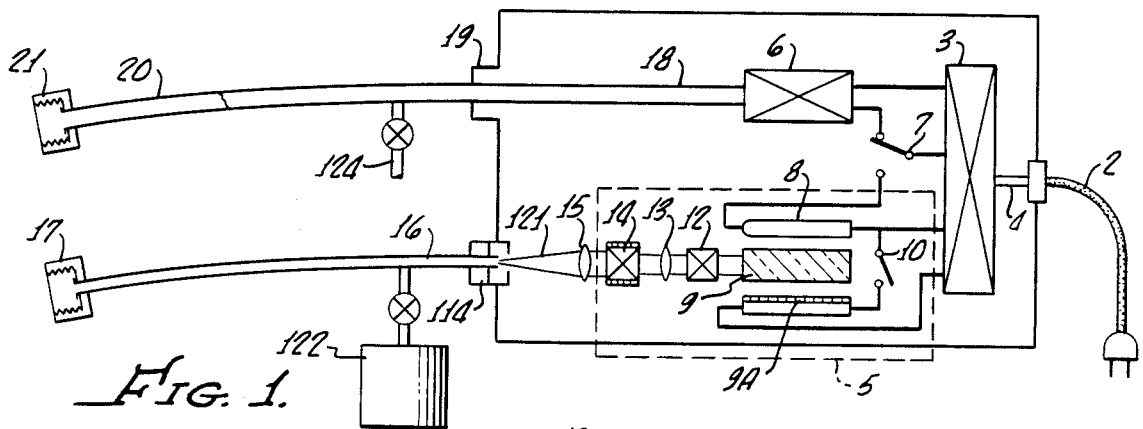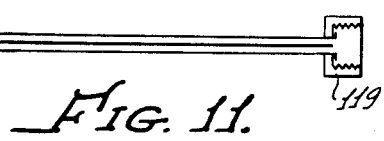

MODULAR INTERCHANGEABLE LASER SYSTEM

The present invention is generally related to a handheld laser-generating system and is more particularly concerned with a system adapted to generate numerous types of laser beams of readily interchangeable modules, each acting as a single stylus to generate the needed type of laser beam for the particular work in hand. The system is further capable of producing a thermally-modulated laser beam, Q-switched laser beam, frequency-doubled laser beam as well as frequency-tripled laser beam, a mode-locked laser beam, and plain laser beam for pointing or demonstration work.

BACKGROUND OF THE INVENTION

This invention relates to an improved embodiment of a laser-beam instrumentation system described in U.S. Pat. No. 4,808,789 (now assigned to the applicant), in which it describes and claims generally semiconductor diode-pumped lasers, while the present invention includes both semiconductor-pumped and flashlamp-pumped (illuminated laser systems. It achieves the many applications of both types of the laser systems and performs rapid and low-cost instrumentations by means of a single laser unit that performs the work of numerous laser systems. The user can obtain long-wavelength, short-wavelength, fine-focus, broad-focus, ultraviolet, visible, or infrared laser beam from a single unit as desired. Ordinarily, these applications require separate laser systems which situation makes it very costly and requires particular space for keeping them. In contrast, this invention is a single unit which provides the characteristics of all these various laser systems in a single unit by merely interchanging the modules thereof.

The present invention has numerous other improvements over the preceding patented invention in that the entire system consists of a single instrumentation unit of numerous operations and applications. As stated, the system further includes the functions of more than a dozen conventional laser systems in a single unitary instrumentation system by interchanging the modules; that is, removing a module from one unit and inserting in into another unit to form a new type of laser-generating device in the infrared, visible, ultraviolet and even longer-wavelength x-ray radiation, depending on the module inserted into the system. Furthermore, the system particularly employs semiconductor diode lasers for the operative laser beam, or for optically pumping (illuminating) a solid-state laser rod selected from a group of laser rods characterized by ruby, neodymium-YAG, neodymium-glass, lithium-sapphire, alexandrite, and the like. In addition, the system console is adapted to accept any solid-state laser generator or any gas laser including helium-neon, and ion lasers such as argon laser, krypton laser, xenon laser, or molecular lasers such as a carbon dioxde laser or excimer laser. These laser systems readily can be inserted in the console or housing that includes the alternating-current rectifier and the control units for both the current and radiation producing sections such as those shown in FIG. 1.

The present invention further exhibits much improvement in efficiency of laser production over conventional laser systems, since it is generally provided with very efficient radiation emitters characterized by semiconduxtor giodes. The radiation emitted from the diodes is pure, stable, unadulterated with any impurities, as the general conventional-type lasers have the tendency to be occasionally bearing pollutant impurities. The present invention further greatly reduces the tendency of emitting heat from the laser generator as common laser systems do and need cooling by means of circulating air, water, or other fluid means, since heat reduces the laser emission efficiency. The service life of a flashlamp (of conventional laser systems) used for pumping the conventional laser systems is also short, typically 400 to 600 hours using the most efficient flashlamp, while diode-pump lifetime ranges more than 100,000 hours. These characteristics of the optical pumping lamp (flashlamp) make the conventional laser bulky and costly to produce, while the present diode-laser pumping system is small in size, compact, and relatively less costly to manufacture. Accordingly, the present solid-state laser production techniques are too wasteful in energy utilization, making the laser system very costly for employment in many technical applications.

The typical laser diodes that are employed in the present invention are: gallium arsenide (GaAs) which typically emits at 8000 angstroms, gallium-aluminum-arsenide (GaAIAs) which emits at 7500 to 9050 angstroms, indium-gallium-aesenic-phosphide (InGaAsP) emitting at 11,000 to 16,000 angstroms in the infrared, gallium-indium-aluminum-phosphide (GaInAlP) emitting at 6700 to 6800 angstroms, and their derivatives. There are still other diode lasers which are hybrids of these diode ingredients, and operate at various wavelengths depending on the power level applied for their emission. These diodes can be operated continuously or in pulsed modes, depending on the character of the circuit in which they are operating. Each of these modes has specific advantages and is selected for use in the different modules in the present laser system.

The diode laser further offers a conversion efficiency of 25 to 40 percent. This is to say that an input power of, for instance, 10 watts can produce 2.5 to 4 watts of laser radiation from the laser rod, because the radiation compatibility of the diode can be modulated to that of the laser rod by temperature-conditioning the diode. Additional advantages of a diode laser pump over the flashlamp is that the radiation from the diode laser can be very pure $TEM_{oo}$, thus matching the operation mode of the laser rod. $TEM_{oo}$ operational mode is the fundamental performance format of a laser element and is derived from the phrase "Transverse Electromagnetic Mode", simulating a gaussian operational format, which is a most efficient performance mode of a laser system.

Furthermore, the thermal problems dominant in flashlamp-pumped systems are alleviated in diode-pumped laser systems, and inherent cooling operations are not difficult to achieve by the use of electrothermal (Peltier Effect) coolers, which are tiny in size and only require a small amount of current to operate, rather than water or air-cooling scheme necessary in conventional flashlamp-pumped process. Thermal birefringence effects and possible thermal focusing problems that reduce the laser-beam emission in the laser rod are also eliminated in diode-pumping mode. An important characteristic of the laser diode in its capability of being modulated easily at high speeds with high-amplitude stabilization that is imparted to the laser rod by the diode performance. An array of diodes operating in unison on a single microelectronic chip produce a cumulative radiant energy which can be focused with a focusing lens on the optical aperture (cross-sectional area) of an optical fiber for transmission of the laser beam. Thus, a very high energy from the diode array can be transferred through a fiberoptic cable to a remotely-located laser rod (as shown in one version of this invention). This type of laser embodiment can enhance the reduction in the size of the laserhead, as achieved in each of the modular embodiments shown in the drawings; furthermore, a small heatsink is provided in the laserhead to cool it when necessary. A heatsink is a highly thermoconductive material, such as a silver-coated thin sheet of nickel or copper. The system then can be made small, compact, and simple in construction. As will be seen from the drawings, the various modular styluses can be provided with thermal tuning, a harmonic generator (frequency amplifier), a Q-switch, and modelocking. Thus the design problems also are simplified and the system structure becomes simpler and less costly to manufacture.

The modular laser system generally employing the semiconductor diode laser for either optically pumping a solid-state laser rod or for furnishing the usable laser beam with nonlinear crystals (harmonic-wave generators) achieves a wide spectral output frequencies and power levels for a variety of applications, using any one of the different modular formats inherent to the present system. The output laser beam being principally diffraction-limited, $TEM_{oo}$, and gaussian at all times. Because of the high efficiency of diode-laser performance, either as an optical pump source or as an emitter of pure laser radiation, and having the ability to be tuned by the temperature of the diode emitter, the system can generally achieve energy output rates of several orders of magnitude over the flashlamp-pumped conventional lasers. The resonant cavity thus can develop an extremely high-quality laser radiation. To add to these advantageous qualities, the system further can transmit therethrough a gaseous element for use in microelectronic processing, conventional industrial processing, in medical surgery and treatment, and military nonlethal applications.

SUMMARY OF THE INVENTION

Having briefly described the many advantages and applications of the present invention over the existing diode-pumped or flashlamp-pumped laser systems, the specific and principal advantages of the present invention may be summerized as follows:

To achieve a variety of performance at high efficiency of the present invention, the principal object of the invention resides in the incorporation of a modular structure with the state-of-the-art diodes or diode arrays to generate any type of high-quality-wavelength laser beam merely by removing a modular section and replacing it by another desired modular section of the system to create emission of the desired laser radiation.

A further object of the invention is to provide a hand-held stylus made up of modular sections easily interchangeable with other modular sections adapted to readily fit in place of the removed section to produce a desired performance characteristic.

A still further object of the invention is to provide each of the modular sections with means to produce a specific function by the combination with another modular section in the stylus to bring about a new optical phenomenon applicable to the work in hand or under processing. Such a combination of functional elements enhance the capability of the system to achieve a variety of applications in a single and compact laser unit.

Another advantage of the invention resides in its capability to have the laser radiation produced in the system to be easily converted from one frequency into another in the same unit without making cumbersome attachment from an outside source.

Another advantage of the invention is the provision of a sectional module adapted with a harmonic generator which receives the emitted radiation from the diode laser and doubles or triples its frequency in the system prior to the emergence of the laser beam from the system stylus This operation converts the infrared radiation from the diode source into a visible radiation or the visible radiation into an ultraviolet radiation essential in the cauterization of tissue in medical surgery or in curing chemical compounds used in microelectronic circuit components and dental ceramic bonding.

A further advantage of the invention is the provision of a laser generator in one species of the system, located remotely from the operative stylus, by the use of a fiberoptic radiation conduit between the source of the laser radiation and the stylus where the laser beam is optically shaped, modified (frequency doubled) or 0-switched and directed by an optical element to an externally-located workpiece to be processed thereby.

A still other object of the invention is to transmit through the laser system a gaseous element together with the laser beam to the site where processing is being accomplished.

A distinct advantage of the invention is the provision of a variable-position optical lens module which varies the focal intensity of the laser beam at the point of contact with the workpiece where the laser-processing is being performed, since some materials require a very intense laser beam (fine focus) intensity to be processed, such as welding blood vessels, thermally curing a dental ceramic over the enamel or evaporating a tiny spot of material from a microcircuit element on a circuit board. A gentle heat is obtained by defocusing the laser beam.

Other objects and advantages of the invention will become more apparent from the specification taken in conjunction with the accompanying drawings, in which:

FIG. 1 is a general view of the laser system containing the input current section, a control means for adjusting the amount of current energy, a flexible conduit for transmitting the current to the laser-generating element, means adapted to receive a conventional laser generator, means for shaping and focusing the laser beam on a fiberoptic conduit with one end attached to the wall connector of the laser system and disposed in the path of the laser beam issuing from a conventional laser radiation device therein.

Figure 4:
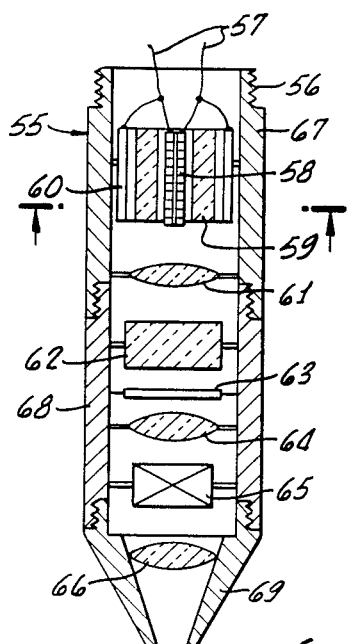

FIG. 4 is another embodiment of the invention wherein the diode-array pumping means is located in a tubular lasent crystal for conserving the entire radiation from the diode-array pumping means, a thermoelectric means to temperature modulate the diode-array beam for making it compatible with the tubular lasent crystal, a harmonic generator to multiply the frequency of the emitted laser radiation thereof, and related optical focusing elements modularly constructed into the stylus.

Figure 5:
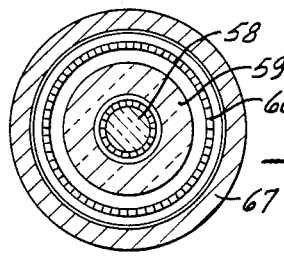

FIG. 5 is the cross-sectional view taken at 5-5'.

Figure 6:
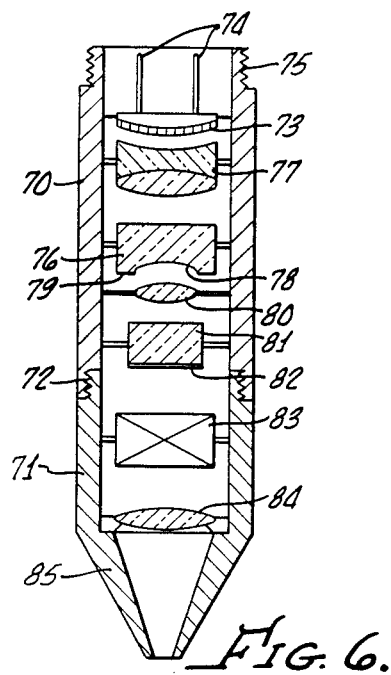

FIG. 6 is a modular embodiment of the invention wherein the diode-pumped laser radiation is frequency-doubled and Q-switched.

FIG. 7 shows a stylus having therein a laser generator consisting of two semicircular elongated rods with their flat surfaces coated with a dichroic material to act as reflectors and to amplify the laser produced therein. In an attached module, the stylus contains a harmonic generator for amplification of the laser beam produced by the semicircular rods.

FIG. 8 is the cross-sectional view of the stylus taken at 8—8'.

FIG. 9 is a sectional view of a modular stylus having a novel laser-generating and amplifying means with a nonlinear crystal (harmonic generator) to multiply the output laser frequency.

FIG. 10 is a sectional view of a fiberscope adapted to be attached to each of the modular styluses shown in FIGS. 2, 3, 4, 6, 7, and 9, including to the connector means of the modular housing shown in FIG. 1.

FIG. 11 is a fiberoptic laser-transmitting conduit, one end of which couples to the coniform end portion of the stylus shown in FIG. 7, as well as to the coupler 114 on one wall of housing 1 shown in FIG. 1.

The modular styluses shown in FIGS. 2, 3, 4, 6, 7, and 9 receive their respective electric current energy from the current-conducting conduit 20 shown in FIG. 1, the amount of the energy is controlled by the current-control means 6 disposed therein.

DETAILED DESCRIPTION OF THE INVENTION

Referring to the drawing shown in FIG. 1, the numeral 1 is a modular housing of a consol, receiving a 110-volt alternating current from an external source through the cable 2 which leads into a conventional current-rectifying means 3 through the cable 4. The current rectifier 3 rectifies the alternating current and furnishes a rectified direct current to the current control section 6 in the laser-generating section 5. The current control section 6 has a conventional control means to transmit a measured amount of current to the cable 18 furnishing power to all styluses in the laser system through the switch means 7, which also supplies a controlled current from section 3 to the laser-generating section 5. The laser-generating section 5 comprises the flashlamp 8 which optically pumps the laser rod 9 to emission of laser radiation.

In case the operator desires to pump the laser rod 9 by means of the semiconductor diode arrays 9A he closes the switch 10 to the diode pump circuit as shown. This action applies a pump current of different characteristic from that furnished by the flashlamp 8; the diode pump radiation is both pure and gaussian in character and is compatible with any laser rod 9. Furthermore, the laser rod 9 can be characterized by any one of the laser rods of neodymium-YAG, neodymium-glass, erbium-YAG, titanium-sapphire, ruby, alexandrite, and the like.

The emitted laser beam from the laser rod 9 passes as beam 11 into a harmonic-wave generator (frequency multiplier) 12, wherein the beam frequency is doubled to increase the photonic energy, such as changing an infrared beam into a visible laser beam. The frequency-doubled laser beam impinges on an optical lens 13 which focuses the beam on a conventional Q-switching device 14 (wavelength amplifying device, if present and desired), from which the laser beam projects on a focusing lens 15, which directs the beam to a fiberoptic cable 16. The fiberoptic cable 16 may be a single fiber or a plurality of fibers, depending how much laser beam need be transmitted therethrough. The fiberoptic cable 16 terminates in a threaded plug 17 which may be connected to any one of the modular sections from the styluses (handheld devices) shown in FIGS. 2, 3, 4, 6, 7, and 9.

The section 6 is a commercial current-control means and furnishes a controlled amount of direct current from rectifier 3 to any one of the modular styluses hereinabove referenced, and to be described in more detail as the description progresses. This current is transmitted through the cable 18 to a connector means 19 located in the wall of the cabinet or console housing 1. From this connector 19 the current is transmitted through a flexible cable 20 to any one of the styluses, by plugging to them through the universal connector 21, which is adapted to fit each of the modular styluses at the upper threaded ends shown in FIGS. 2, 3, 4, 6, 7, and 9. Each of the styluses will be described more fully in the ensuing sections of the specification.

Figure 2:
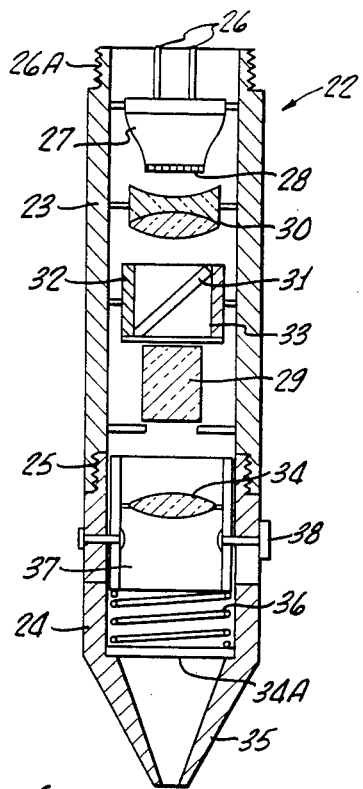
FIG. 2 is the longitudinal sectional view of the stylus of the laser system with self-contained laser-generating and beam-amplifying means, and a variable-position beam-shaping element for focusing the laser beam on the workpiece.

Starting with the stylus means 22, shown in FIG. 2, the device consists of the modular sections 23 and 24 fitted together at the threaded portion 25. This system is supplied by an energizing current furnished from the cable 20, whose coupling 21 connects to section 26A and leads the current through the contact points 26 into the semiconductor means 27 with an array of diodes 28, which projects a laser beam when energized unto the lasing element (bar) 29 through the collimator 30 and a dichroic element 31. The laser beam partially passes through the element 31 and partially reflects to a reflector (mirror) 32, which, in turn, reflects the beam to mirror 33, from which the beam partially reflects and impinges on the lasing element 29 and partially reflect to mirror 32 by passing through the dichroic element 31. The back and forth reflections of the laser beam between morrors 31 and 32 causes the beam to be amplified in the optically resonant cavity. Thus, the final beam is an amplified laser radiation; this action increases the radiant emission of the lasing bar 29.

The lasing bar 29 then becomes stimulated (by radiant energy) and produces its own characteristic laser radiation. The laser beam from the bar 29 projects upon a position-variable optical lens 34 which focuses the laser beam on an externally located object to be processed, after passing through the transparent plate 34A and section 35. The spring member 36 biases the housing 37 and hence the lens 34 located therein. The thumb button 38 positions the housing 37 supporting the lens 34 to any focal position desired by the operator of the device. This type of arrangement is necessary, for instance, in medical surgery where the fine focal point cuts the tissue and the defocused focal point cauterizes the tissue, as when deemed necessary. The lasing bar 29 is partially coated at one end 39 for internal photonic resonance and stimulation of the laser radiation therein.

Figure 3:
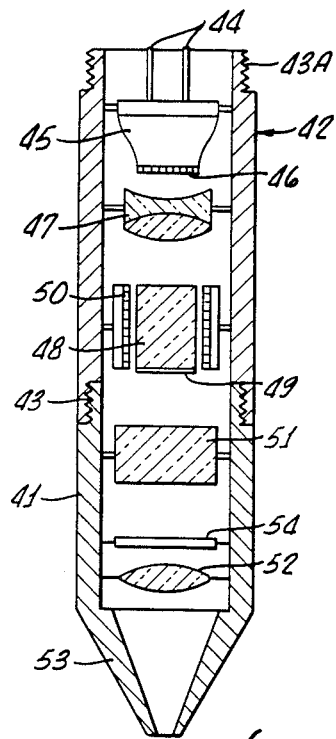
FIG. 3 is another view of the modular laser-beam generator with a harmonic-beam generator, and a stationary beam-focusing element.

In FIG. 3, the modular sections 40 and 41 form the stylus 42 structure by fitting theretogether at the threaded area 43. Similar to stylus 22, this embodiment receives a controlled current through cable 20 and coupler 21, which couples to stylus 42 at the threaded section 43A and transfers the current to the system through electric contacts 44 to a laser diode means 45 with diode arrays 46. When the diode array 46 is energized by the incoming current, it produces a characteristic bright laser radiation, which passes through the beam collimator 47 and impinges on the laser rod 48. The laser rod 48 is partially coated at 49 to cause beam resonance and amplification when it is stimulated (pumped) by the incident radiation from the diode array at 46. The laser rod is further stimulated by the peripherally positioned diode arrays 50, thus producing a copious, high-intensity laser radiation. The radiation from the laser rod 50 then projects out and impinges on a harmonic generator 51 when the module 41 is connected thereto, as shown in FIG. 3. The frequency of the incident beam on the harmonic generator 51 becomes doubled (amplified) thereby and the beam projects upon a focusing lens 52 which directs the laser beam through the coniform section 53 on an object located externally thereto. The transparent dichroic plate 54 is used to cause resonance and amplification of the laser beam formed in harmonic generator 51.

The embodiment 55 shown in FIG. 4 likewise is fitted to the coupler 21 at the threaded upper section 56. The coupler 21 transfers an energizing current to stylus 55 through electrical contacts 57, which are connected to the diode arrays 58 positioned centrally to a tubular lasing bar 59 surrounded by a thermoelectric element 60, peripherally thereof, for temperature-conditioning the laser generator 59 as well as modulating the laser diodes 58 to make their radiant beam compatible with the laser bar 59 characteristics: the latter condition aids in the efficient coupling of the pump radiation from the diode arrays 58 with the laser bar 59.

The resulting laser radiation from the lasing bar 59 is directed on a focusing lens 61, which projects the beam upon a harmonic generator 62 for frequency amplification, aided by a dichroic plate 63. The frequency-multiplied laser beam from the harmonic generator 62 passes through the optical lens 64 and is directed thereby at a conventional-type Q-switching means 65, which produces a very high power with extremely short pulses. The Q-switched laser beam then becomes incident on the output focusing lens 66, which focuses the laser beam on the workpiece to be processed. This stylus consists of the modular sections 67, 68, and 69, any one of which can be interchanged with the respective sections from styluses 22 and 42. FIG. 5 is a cross sectional view of the stylus taken at section designated by 5-5'.

The stylus shown in FIG. 6 consists of two modules 70 and 71 connected together at the threaded portion 72. The module 70 contains a diode or a diode array 73 having electrical contacts 74 which receive energizing current from the flexible cable 20 when the universal connector 21 is screwed on the threaded end 75 of modulae 70. The received current energizes the diode array 73 to emission of a laser radiation which pumps the laser element 76 receiving the diode radiation through the beam collimator 77. The laser element 76 is a circular rod with a concave cavity 78 at one surface with a circular rim 79 which is coated with a highly reflective substance (mirror) to form a radiation resonating means for stimulating laser radiation from the rod 76.

The resulting stimulated laser beam emerges from the cavity 78, passes through the converging leans 80 and impinges on a harmonic generator 81 with partially transmissive coating 82, which acts as the resonator of the laser beam stimulated in the harmonic generator 81. The frequency-multiplied laser beam in the harmonic generator 81 emerges from it and becomes incident on a conventional Kerr-cell Q-switching means 83, wherein the beam acquires a high power short-pulse format. The Q-switched beam from the means 83 projects on a converging lens 84 which focuses the Q-switched and frequency multiplied laser beam on a workpiece located externally to the coniform section 85.

The modular embodiment shown in FIG. 7 comprises the module 86 and the module 07 connected together at the threaded portion 88. When the stylus 86 is coupled to the upper threaded end 88A to coupler 21, it receives a current through the contacts 89 and 90 to energize the diode arrays 91 and 92, which optically pump the laser elements 93 and 94 to emission of laser radiation. The elements 93 and 94 are semicircular laser-generating bars, with their flat surfaces at 93 coated with a dichroic optical material to form a beam reflecting surface therebetween to cause the the radiation emitted by the bars 93 and 94 to be amplified therein.

The stimulated radiation in the laser generating bars 93 and 94 is projected on the optical collimator 96 and then directed at a harmonic generator 97 in module 87; the harmonic generator 97 amplifies the frequency of the laser beam and projects it on a focusing lens 98 located at the base of the coniform section 99 of module 87. The lens 98 then converges the laser beam through the section 99 upon a workpiece positioned externally to said module 87. The threaded end 100 of module 87 is adapted to be connected to a fiberoptic conduit that will be described in an ensuing section of this description.

The stylus shown in FIG. 9 is made up of module 101 and module 102. The electric current enters the stylus at module 101 through contacts 103 and 104. The current energizes the laser diode array 105, the radiation from which optically pumps the laser element 106 axially thereof as well as peripherally to it by means of the coniform reflector 107 which bends the perpendicular beam incident on its 45° surface through a 90° angle, as shown by vertical and horizontal lines. This latter action causes the laser rod 106 to be flooded with laser radiation, causing the rod 106 to emit a copious amount of laser radiation, making the device one of the most powerful laser emitters The partial coating 108 at one end of the rod 106 acts to excite resonation therein.

The emitted laser beam from the laser element 106 is directed on a harmonic generator 109 through the converging lens 110. The harmonic generator 109 has a dichroic reflector 109A and frequency-multiplies the laser beam and projects it on a converging lens 110A, which converges the beam through the coniform section 111 and focuses it on an externally located workpiece. The lens 110A is supported by means of a peripheral flange 110B, which is biased by a spring 110C whereby the lens 110A can be moved down and up by means of a thumb button 110D, when the operator deems it necessary.

FIG. 10 represents a lightguide 112, which attaches at coupler 113 either to the threaded section 100 of stylus 86 or to the coupler 114 located in the wall of the laser system cabinet 1. The lightguide has one or more optical fibers 115 to transmit a visible laser beam either from the module 87 or from the laser source 9, shown in FIG. 1, unto the workpiece through the objective lens 116. A second bunch of coherent fiber bundle 117 conducts the image of the workpiece to an eyepiece 118 during cutting or drilling a material or incising a human anatomical structure during surgery. The lightguide 112 is not drawn to scale in order to show the internal structures clearly.

The socket 119 of fiberoptic conduit 120 with its optical fiber 125 plugs either to socket at 114 to transmit the laser beam 121 to a workpiece or to the threaded end 100 of module 87 to transmit the laser beam from the stylus 86 during a medical treatment of an anatomical organ. (It must be noted here that the module 87 can be connected to any one of the other styluses to obtain the expected laser team from the chosen stylus.) The functions and operations of all the modules and related accessories will be fully described under the heading Operation of the System. Both the cable 16 and cable 20 are adapted to be connected to a source of gaseous element contained in a tank 122 respectively at controlled connections 123 and 124.

APPLICATIONS OF THE SYSTEMS

* Industrial Processing—Cutting, drilling, welding, scribing, resistance trimming, and marking.

* Medical Use—Surgery and treatment, such as incision of tissues, ablating ophthalmic tissue, disintegrating cardiac artery plaques, etc.

* Dental Treatment—Drilling enamel, treating gingivitis, cauterizing pulp in tooth cavity, therapeutic applications, etc.

* Metrologic Use—measuring dimensions and distances, aligning structures, pointing to important sites, gauging, pollution measurement, fingerprint detection and interpretation, supermarket checkout, etc.

* Military Systems—Rangefinding, target designation, weapon simulation, security surveillance, etc.

* Aeronautical Applications—Data transmission, voice transmission, detection of aerial targets, and similar missions.

* Automotive Devices—Instrument panel indicators, engine condition indicator, collision preventive preindications, radar beam detection.

* Holography—Making 3-dimensional images for quality assurance study, medical treatment study, etc.

* Research—For research of numerous laboratory and factory instrumentations and systems and similar disciplinary projects.

OPERATION OF THE SYSTEM

The modular interchangeable laser system may be considered a universal laser-producing apparatus with ultimate capabilities of performing the functions of numerous laser units of different modes of operation. For instance, the laser generator 9 in FIG. 1 could be an ion laser, such as an argon or krypton laser; molecular laser such as a carbon dioxide laser; solid-state laser such as a neodymium-YAG, neodymium glass, titanium-sapphire, etc.; excimers such as argon fluoride, xenon fluoride, etc.; metal-vapor lasers such as gold-vapor laser or copper-vapor laser; or, an array of semiconductor laser diodes such as gallium arsenide, gallium-arsenide-phosphide, and the like. It could be any one of dozens of lasers now commercially in use. The operator of the system may choose any one of these lasers for the particular work in hand.

In addition to the types of lasers, the output laser beam from the system could be frequency-doubled, Q-switched, modelocked or employed as any combination of these modes. Thus, section 5 of FIG. 1 can be connected to any one of the modules 24, 41, 68, 71, 87, 69, and 102 assembled in the various styluses given. For lack of space, not all combinations of modules and styluses can be presented herein; the user of the system can easily determine the combination of modules for the specific laser-processing under consideration.

Furthermore, any required gaseous material from a tank, such as the tank 122 can be connected to the radiation conduit or electric current conduit for transmission through any selected module to the workpiece site. Because the operation of the system is very flexible, the operator of the system will have under his command any type of laser, mode of operation, radiant intensity, and focal size for the particular application in hand. No reactive gases, such as fluorine, chlorine, oxygen, or the combinations thereof should be employed because of their chemical interaction with the metallic, glass, or plastic materials contained in the styluses and modules.

In the event one desires to use a plane argon-ion laser or helium-neon laser, the section 5 is fitted with only the conventional argon-ion or helium-neon laser. The radiation is then conducted through the lens 15 which focuses it on the cross-sectional area of the fiberoptic cable 16. The connector 17 is connected to module 24 or module 69 in case the focal area is to be varied during processing the workpiece. If Q-switching is required, then the module 71 is connected to coupler 17. If frequency-doubling is necessary, the module 47 is connected to the coupling 17. In case the beam must have high intensity with the frequency-doubling, then the stylus 42 shown in FIG. 3 is used. The module 23 of stylus 22 may be employed with module 68 if a high-intensity laser beam which is also frequency-doubled and Q-switched. This interchange of modules can go on and on to several dozen combinations. However, when a stylus is used, with any combination of modules, the stylus must be connected to the coupler 21 for its power supply.

The conduit shown in FIG. 10 is usually connected at its coupler end 113 to the threaded section 100 of module 99. The module 86 of FIG. 7 can be replaced by module 101, 23, 67, 86, 40, or 70, as desired. Similarly, the conduit 120 can be connected to the threaded section 100 or to coupling 114 of console 1. The conduit 120 is generally used for medical exploration of various organs by inserting the single optical fiber 125 into the cavity of the organ to be explored. The conduit 112 is similarly employed for medical exploration; the size of the conduit shown in the figure is not proportional or to scale for reasons of clarity of exhibiting the structures contained therein.

I claim:

1. A modular interchangeable laser system, comprising a modular housing means provided therein with an interchangeable radiation source energized by an electric current supply means having a current-control means and a radiation-generator control means independently operable by a double-throw switch means disposed in said housing said modular housing means having a radiation outlet means and a current outlet means being positioned side by side in one wall thereof and respectively connected to a radiation-conduit means and to a current-carrying conduit means, with said current outlet means being in electrical contact with said electric current supply means; said current-carrying conduit means provided with coupling means adapted to be connected to one end of a handheld modular stylus having therein a laser beam-generating and amplifying means energized by the current from said current-carrying conduit means, and a laser-beam spectrum modifying means disposed therein in the path of the laser beam emitted by the laser beam-generating means to modify and project said laser beam to the exterior of said modular stylus; said radiation conduit means being in optical connection at one end thereof with said interchangeable radiation source, through said radiation outlet means and at the other end being adapted with means to be connected to a modular section of a modular stylus to form a unitary laser system theretogether; a peripheral spacing within each of said conduits and in said modular stylus adapted to receive a gaseous element from an external source connected to said conduits for transmittal of said gaseous element through either of said conduits into said modular stylus for conduction therethrough to the exterior thereof during laser-processing a workpiece.

2. A modular interchangeable laser system as defined in claim 1, wherein said interchangeable radiation source is a laser generator consisting of a solid-state laser-emitting element optically pumped by a radiant means disposed therein for optical excitation of said element.

3. A modular interchangeable laser system as described in claim 2, wherein said solid-state laser-emitting element is one of the laser-generating rods selected from the group consisting of neodymium-YAG, neodymium-glass, alexandrite, titanium-sapphire, ruby, and erbium-YAG.

4. A modular interchangeable laser system as described in claim 2, wherein said radiant means is an electric flashlamp selected from the group consisting of a nitrogen discharge tube, argon-ion laser, and a thermoinic light source.

5. A modular interchangeable laser system as described in claim 2, wherein said radiant means is a semiconductor laser diode selected from the group consisting of aluminum-gallium-arsenide, gallium-arsenide, gallium-aluminum-arsenide-phosphide, and their derivatives.

6. A modular interchangeable laser system as described in claim 1, wherein said modular housing is adapted with means to receive the coupling of a fiberoptic cable for attachment thereof to said means and to transmit into said fiberoptic cable a laser radiation produced by a laser-beam generator disposed in said modular housing for transmission of said laser-beam radiation from said cable to the site of a human anatomical organ through a small-diameter optical fiber continuous with said fiberoptic cable and projecting beyond the sheathing of the fiber-optic cable for several centimeters therefrom.

7. A modular interchangeable laser system as described in claim 6, wherein said modular housing contains a removable Q-switching means and a replaceable modular harmonic generator, both of which are optically connected to the laser-beam generator disposed therein and are adapted with means to be removable whereby only the laser beam from said laser-beam generator is available to the optical fiber in the fiberoptic cable attached to said modular housing for transmission of said laser beam to a workpiece located externally to said modular housing.

8. A modular interchangeable laser system as defined in claim 1, wherein said electric current supply means is a source of rectified direct current originated from a 110-volt alternating current furnished into the rectifier of the modular housing from a conventional power source.

9. A modular interchangeable laser system as defined in claim 1, wherein said current-control means is a double-throw switch means to channel the electric current to two different circuit channels therein, one of which channels being a power transmission means and the other channel being a radiation transmission means.

10. A modular interchangeable laser system as defined in claim 1, wherein said handheld modular stylus comprises a plurality of modules interlinked together to form a unitary laser system having therein a modular housing having means adapted at one end thereof for connection to an external source of current, the opposite end of said housing being coniform with an axial opening therethrough; said stylus having therein a radiant source connected to said source of current for energization of said radiant source to emission of a laser beam, a wave length modifying means positioned in the path of said laser beam to modify the frequency of said laser beam and to project the wavelength modified laser beam upon an optical means to convergently project said wavelength modified laser beam to the exterior of said modular stylus through the coniform end of said stylus thereof.

11. A modular interchangeable laser system as described in claim 1, comprising a modular stylus adapted at one end with means to receive an electric current from an external source, a semiconductor diode array receiving a current from said source of electric current to emit a laser beam, and a beam-shaping optical means disposed adjacent thereto to shape said laser beam and to project it on a solid-state laser-generating element positioned in the path of said laser beam and receiving a laser-stimulating energy therefrom; said laser-generating element having an array of semiconductor diodes disposed peripherally thereof to receive an amplifying laser energy from said diode array to form therein a cumulative laser radiation, a harmonic-wave generator positioned in adjacence to said solid-state laser element to collect said cumulative laser radiation therefrom to modify the frequency of the radiation thereof and to project the frequency-modified laser beam on a converging optical lens through a beam-resonating plate disposed therebetween to the exterior of said stylus through a hollow coniform section formed at the terminal end of said stylus.

12. A modular interchangeable laser system as described in claim 1, comprising a tubular stylus formed by a plurality of modules fitted together to form a unitary laser system; one of said modules at one end of said stylus having a source of electric current and a laser-generating means disposed adjacent thereto receiving a current therefrom for energization of said laser-generating means, and a thermoelectric means disposed adjacently thereto to temperature-condition said laser-generating means emitting a laser beam and projecting it upon a harmonic generator through a beam-concentrating means positioned therebetween; and optical plate in adjacent relation to said harmonic generator to cause resonance and thereby amplification of the laser-beam frequency modified by said harmonic generator and to direct it upon an optical lens to project it on a Q-switching means positioned in the path of the frequency-modified laser beam to amplify the optical power thereof and to direct the high-power laser beam to the exterior of said stylus through a converging lens disposed in the output coniform end of said stylus.

13. A modular interchangeable laser system as defined in claim 12, wherein said laser-generating means comprises a tubular solid-state lasing bar having a laser-emitting source disposed within the tubular section thereof for receiving from said laser-emitting source a laser-stimulating energy to become excited thereby to emission of a high-power laser radiation, and a thermoelectric means disposed peripherally to said tubular solid-state lasing bar to temperature modulate said laser-generating means.

14. A modular interchangeable laser system as defined in claim 12, wherein said stylus is made up of three modules, one of which contains a laser-generating means, the second module contains a laser-beam modifying means disposed in the path of the laser beam emanating from the laser-generating means to modify the laser beam thereof, and a third module contains an optical means to direct said laser beam on a workpiece; any one of the three modules in said stylus can be removed and substituted by other modules from the modular section of the stylus in said modular interchangeable laser system.

15. A modular interchangeable laser system as defined in claim 14, wherein said laser-beam modifying means in said second module comprises a frequency-amplifying means, an optical plate partially coated with a reflecting means to produce resonance of the laser beam therein, a converging lens to receive the frequency-amplified laser beam from said laser-beam modifying means and to converge said laser beam upon a Q-switching means to increase the pulsar power of said laser beam in said module.

16. A modular interchangeable laser system as defined in claim 1, wherein said modular stylus consists of two modules assembled together to form a unitary device; one of said modules contains a high-power laser-generating means and the other module a position-variable optical lens having a housing biased by means of a spring and provided with a thunb button attached to said housing and thereby to said lens in said stylus to change the focus intensity of the laser beam projected therefrom upon a workpiece located externally to said housing.

17. A modular interchangeable laser system as defined in claim 16, wherein said high-power laser-generating means comprises a multiple source of laser beam with a dichroic reflecting means disposed therebetween to resonate the laser beam therein by reflection of the combined laser beams between the mirrors disposed diagonally opposite to each other therein.

18. A modular and interchangeable laser system as defined in claim 1, comprising a modular stylus having therein a semiconductor diode array energized by means of an externally furnished current therein to produce a coherent laser radiation, a laser-beam collimating means adjacently disposed to said diode array to collimate the radiation therefrom and to project it on a solid-state laser circular block having a concave section at one surface thereof and an annular area with a reflective coating thereon formed peripherally to said concave section; an optical lens positioned adjacent to said concave section to receive a laser beam from said solid-state laser circular block and transfer it to a harmonic generator to frequency-amplify said laser beam and then project in on a Q-switching means positioned in the path of said laser beam; a converging lens disposed in the radiation output end of said stylus to receive said Q-switched laser beam and to focus it upon a workpiece located externally to said stylus.

19. A modular stylus as defined in claim 18, comprising two modules, one of which containing a laser generating and amplifying means and the other containing a Q-switching and focusing means connected to said first module by means of a threaded section to form a unitary laser-producing means; said Q-switching and focusing means is adapted to be disconnected from its companion module and connected to any other stylus of the modular and interchangeable laser system to Q-switch the laser beam produced in said other stylus.

20. A modular interchangeable laser system as described in claim 1, wherein said modular stylus comprises two modules, one of which is a laser-beam generator means and the other is a laser-beam modifying means having a hollow coniform section for transmission of the laser beam emitted therein to the exterior thereof; said laser-beam generator means comprises two laser rods of semicircular cross section in their axial aspects, each having a flat surface with a dichroic coating thereon and placed face to face for acting as laser-beam reflectors and amplifiers; two semicircular laser emission sources are disposed peripherally to said laser generator means, respectively thereof, to optically pump the semicircular rods when said emission sources are energized by an external current led through one end of said modular stylus; and, a frequency multiplying means with a lens adjacent thereto is disposed in said second module to amplify the frequency of the laser emission therein and direct it externally to said hollow coniform section.

21. A modular interchangeable laser system as described in claim 1, wherein said stylus comprises two modules connected together to form a single handheld unit; one of said modules contains a semiconductor diode array at one end of said stylus and receives an electric current from an external source for energizing thereof to emission of a laser beam; a solid-state laser rod with a conical reflector means fitted therearound disposed axially in adjacent relation to said diode array whereby the laser beam from said diode array optically pumps said laser rod and projects a laser beam on said conical reflector means which being positioned in an angular relation to reflect the laser beam impinging thereon unto said laser rod peripherally thereto for amplification of the laser emission from said laser rod; the second module having therein a laser-beam modifying means and a hollow coniform section, with said laser-beam modifying means receiving the laser beam from said laser rod to multiply the frequency thereof and to convergently project it through said hollow coniform section to the exterior thereof upon a workpiece positioned adjacent thereto.

22. A modular interchangeable laser system as described in claim 19, wherein said laser-beam-modifying means located in the second module of the stylus has a focusing lens and means adapted to hold said focusing lens in an axial aspect to said stylus and adjacent to the hollow coniform section thereof, said focusing lens having a peripheral support means in said second module and a spring means thereunder to retain said focusing lens in an upwardly biased position, and a thumb button on the exterior of the wall of said module and attached to said peripheral support means to move said peripheral support means and thereby said focusing lens to and away from the reduced section of said hollow coniform section to vary the focus position and hence the intensity of the laser-beam focus projected upon a workpiece externally disposed to said coniform section.

23. A modular interchangeable laser system as defined in claim 1, wherein said radiation outlet means optically connected to said interchangeable radiation source is adapted with means to accept one end of a fiberoptic conduit having at its opposite end an optical lens means and an optical fiber optically connected between said lens means and said interchangeable radiation source to transmit a laser beam from said interchangeable radiation source to a workpiece located adjacent to said lens means externally thereof; and a second optical fiber connected at one end thereof, in said fiberoptic conduit, to said lens means to collect visual information from said workpiece and to transmit said visual information to the other end thereof having an optical eyepiece which translates said visual information into a pictorial display whereby an observer at the eyepiece can visually sense the laser-processing events occurring at the workpiece.

24. A modular interchangeable laser system as defined in claim 1, wherein said handheld modular stylus comprises two modules connected together to form a unitary laser device; one of said modules containing therein a laser-beam generating and amplifying means and the other containing therein an optical means positioned in the path of a laser beam emanating from said laser-beam generating and amplifying means to receive and focus said laser beam on a workpiece disposed externally to said handheld modular stylus; said optical means having a support means in said other module and said support means biased by a spring means thereunder and being provided with a thumb button means located on the external periphery of said other module for displacing said optical means in said module to vary its focus position axially to said module.

25. A modular interchangeable laser system as described in claim 1, wherein said interchangeable radiation source is a titanium-sapphire laser rod optically pumped by means of a laser diode array disposed adjacent thereto.

26. A modular interchangeable laser system as defined in claim 1, wherein said interchangeable radiation source is a neodymium-YAG laser rod optically pumped by means of an array of semiconductor laser diodes disposed in adjacence thereof.

27. A modular interchangeable laser system as defined in claim 1, wherein said interchangeable radiation source is an alexandrite laser rod optically pumped by an array of semiconductor laser diodes disposed in adjacent relation to said alexandrite laser rod.

28. A modular interchangeable laser system as described in claim 1, wherein said interchangeable radiation source is a laser-emitting rod optically pumped by means of a radiant lamp means axially disposed to said laser-emitting rod therein.

29. A modular interchangeable laser system as described in claim 1, wherein said interchangeable radiation source is a laser-emitting rod optically pumped by means of a laser-radiation source disposed adjacent thereto and receiving an electric current from a direct-current source located in the modular housing means of said modular interchangeable laser system.

30. A high-intensity modular laser system comprising a stylus having a plurality of optical modules having tubular housings interlinked together for form a unitary laser system; one end of said stylus being adapted to receive an electric current from an external source and its opposite end being coniform with opening therethrough; a semiconductor diode array disposed in said stylus at its end opposite to the coniform section and receiving an energizing current from said source of electric current for emission therefrom of a laser radiation to optically pump a lasing means disposed adjacent thereto and in the path of said laser radiation to stimulate said lasing means to produce a coherent radiation therein, and a laser-beam modifying element positioned axially to said stylus in the path of said coherent radiation to modify said radiation and to project it on an optical element to convergently direct the modified beam of said coherent radiation through said coniform section to the exterior thereof.

* * * * *